United States Patent [19]
Nishimura et al.

[11] Patent Number: 5,655,531
[45] Date of Patent: Aug. 12, 1997

[54] MRI METHOD AND APPARATUS FOR SELECTIVE IMAGE SUPPRESSION OF MATERIAL BASED ON T1 AND T2 RELATION TIMES

[75] Inventors: Dwight G. Nishimura, Palo Alto; Jean H. Brittain, Stanford, both of Calif.

[73] Assignee: The Board of Trustees of the Leland Stanford Junior University, Palo Alto, Calif.

[21] Appl. No.: 441,101

[22] Filed: May 15, 1995

[51] Int. Cl.⁶ .................................................. A61B 5/055
[52] U.S. Cl. ..................... 128/653.2; 324/307; 324/309
[58] Field of Search .................... 128/653.2; 324/307, 324/309

[56] References Cited

U.S. PATENT DOCUMENTS

| | | |
|---|---|---|
| 4,684,892 | 8/1987 | Graumann . |
| 5,248,942 | 9/1993 | Ratzel et al. . |
| 5,565,776 | 10/1996 | Kanazawa . |
| 5,570,019 | 10/1996 | Moonen et al. . |
| 5,588,431 | 12/1996 | Marii et al. . |
| 5,594,336 | 1/1997 | Gullapalli . |

OTHER PUBLICATIONS

Brittain et al., Coronary Antiography With Magnetization-Prepared T2 Contrast, Magnetic Resonance in Medicine in Medicine, vol. 33, No. 5, May 1995, pp. 689–696.

Brittain et al., Three-Dimensional Flow-Independent Peripheral Angiography, SRM, to appear Aug. 1995, 1 page.

Brittain et al., Coronary Angiography with Magnetization-Prepared T2 Contrast, MRM, to appear, 1995.

*Primary Examiner*—Marvin M. Lateef
*Assistant Examiner*—Shawna J. Shaw
*Attorney, Agent, or Firm*—Townsend and Townsend and Crew LLP; Henry K. Woodward

[57] ABSTRACT

The selective imaging of an object having two materials with different relaxation times (T1 or T2) is provided by using a driven equilibrium sequence (T2 weighted preparation sequence) followed by an inversion recovery sequence. In the driven equilibrium sequence the object is placed in a static magnetic field along a longitudinal axis, an excitation pulse is applied to tip nuclei spins into a transverse plane, and at least one refocusing pulse is applied to produce a spin echo having a magnetization component as a function of relaxation time. At least one pulse is then applied to the object to drive the spin echo to an inverted position along the longitudinal axis. A readout excitation is then applied at a later time when the longitudinal magnetization of one material is substantially reduced. In one embodiment, an inversion pulse is applied prior to the T2 weighted preparation sequence.

12 Claims, 5 Drawing Sheets

MRI METHOD AND APPARATUS FOR SELECTIVE IMAGE SUPPRESSION OF MATERIAL BASED ON T1 AND T2 RELATION TIMES

The U.S. Government has rights in the invention pursuant to NIH contract No. 2 R01 HL 39297 with Stanford University.

BACKGROUND OF THE INVENTION

This invention relates generally to magnetic resonance imaging, and more particularly the invention relates to magnetic resonance imaging with selectively suppressed material based on spin-lattice relaxation time (T1) and spin—spin relaxation time (T2).

Magnetic resonance imaging (MRI) is a non-destructive method for the analysis of materials and represents a new approach to medical imaging. It is generally non-invasive and does not involve ionizing radiation. In very general terms, nuclear magnetic moments are excited at specific spin precession frequencies which are proportional to the local magnetic field. The radio-frequency signals resulting from the precession of the spins are received using pick up coils. By manipulating the magnetic fields, an array of signals is provided representing different regions of the volume. These are combined to produce a volumetric image of the nuclear spin density of the body.

Different atomic nuclei can have different magnetic resonance due to differing magnetogyric ratios, $\gamma$. In accordance with the Larmor relationship, the angular frequency $\omega_0$ of nuclei precession is the product of the magnetic field $B_0$ and the magnetogyric ratio, $\gamma$. This allows selective excitation and imaging of different nuclei, and by applying a magnetic gradient to the imaged object, different slices through the object can be selectively excited and imaged.

Additionally, the transverse magnetization is not only related to the specific nuclei that are excited, but also to their motional characteristics manifested by relaxation times. The spin-lattice relaxation time, T1, is equivalent to a regrowth of the longitudinal magnetization following excitation of nuclei with transverse RF magnetic fields. The spin—spin relaxation time, T2, reflects the decay time of a transverse component of free induction signals following excitation.

A variety of techniques have been developed to suppress material in image signals based on a particular physical parameter. This includes the saturation of a chemical shift species using a frequency selective excitation pulse, and the saturation of blood or other moving material via the application of a selective excitation to the blood upstream of the imaging region. Additionally, a preparatory magnetization transfer (MT) excitation has been used to reduce the longitudinal magnetization of species exhibiting greater amounts of MT phenomena. See Hu and Conolly U.S. Pat. No. 5,250,898. Additionally, the T1 and T2 relaxation times have been used in selective imaging. A relatively long preparatory low level RF pulse has been used to saturate longer T2 species. Further, a long echo time, TE, readout can be used to suppress shorter T2 species. Inversion recovery can be used to null a particular T1 species by applying a 180° inversion pulse and timing the ensuing readout to occur when the T1 species is passing through its null point in the longitudinal magnetization recovery. Also, a nonselective driven equilibrium sequence (i.e., T2 weighted preparation sequence) can be used with a long echo time TE readout to suppress shorter T2 species.

The present invention is directed to selective suppression of material depending on the material's T1 and T2 relaxation times.

SUMMARY OF THE INVENTION

In accordance with the present invention a method and apparatus is provided for selectively suppressing magnetic resonance signals in an object having at least two materials therein with different relaxation times, either T1 or T2 or both. The object is first placed in a static magnetic field oriented along a longitudinal axis. A first excitation pulse is then applied to the object to tip nuclei spins into a transverse plane. Thereafter, at least one refocusing pulse is applied to the object to produce a spin echo at a time TE. Thereafter, at least one pulse is applied to the object to drive the magnetization to an inverted position along the longitudinal axis. A readout excitation is then applied at a time TI thereafter when the longitudinal component of one material is nulled or substantially reduced relative to another material to be imaged.

In one embodiment, after the spin echo is produced at the time TE, an excitation pulse is applied to the object to drive the spin echo to the positive longitudinal axis, and then another excitation pulse is applied to invert the magnetization component by 180°. In another embodiment, after the spin echo is produced at time TE, a single excitation pulse is applied to invert the magnetization component along the longitudinal axis.

In another embodiment, the inversion pulse is applied prior to the T2 weighted preparation sequence so that the T2-weighted magnetization is driven to the negative longitudinal axis, as desired, instead of the positive (+) longitudinal axis.

The invention and objects and features thereof will be more readily apparent from the following detailed description and appended claims when taken with the drawings.

DESCRIPTION OF THE ILLUSTRATIVE EMBODIMENTS

Figure 1A:
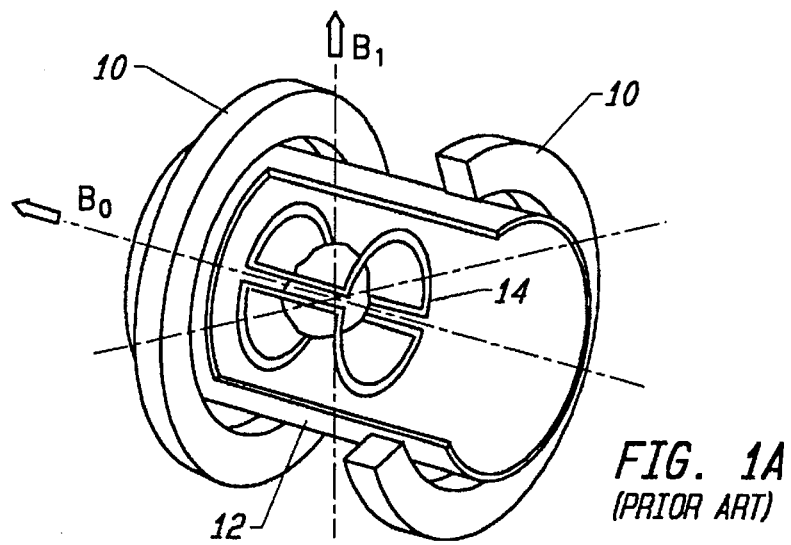
FIGS. 1A–1D illustrate the arrangement of MRI apparatus and magnetic fields generated therein in carrying out invention.
Figure 1B:
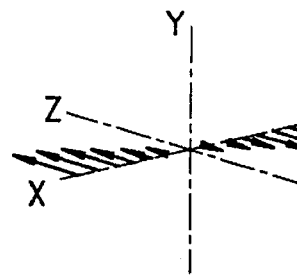
Figure 1C:
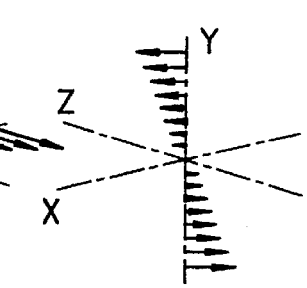
Figure 1D:
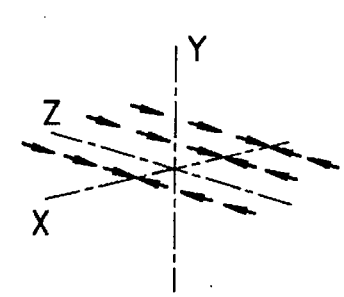

Referring now to the drawings, FIG. 1A is a perspective view partially in section illustrating coil apparatus in an MRI imaging system, and FIGS. 1B–1D illustrate field gradients which can be produced in the apparatus of FIG. 1A. Briefly, the uniform static field $B_0$ is generated by the magnet comprising the coil pair 10. A gradient field $G_x$ is generated by a complex gradient coil set which can be wound on the cylinder 12. An RF field $B_1$ is generated by saddle coil 14. A patient undergoing imaging would be positioned along the longitudinal Z axis within the saddle coil 14.

In FIG. 1B an X gradient field is shown which is parallel to the static field $B_0$ and varies linearly with distance along the X axis but does not vary with distance along the Y and Z axes. FIGS. 1C and 1D are similar representations of the Y gradient and Z gradient fields, respectively.

Figure 2:
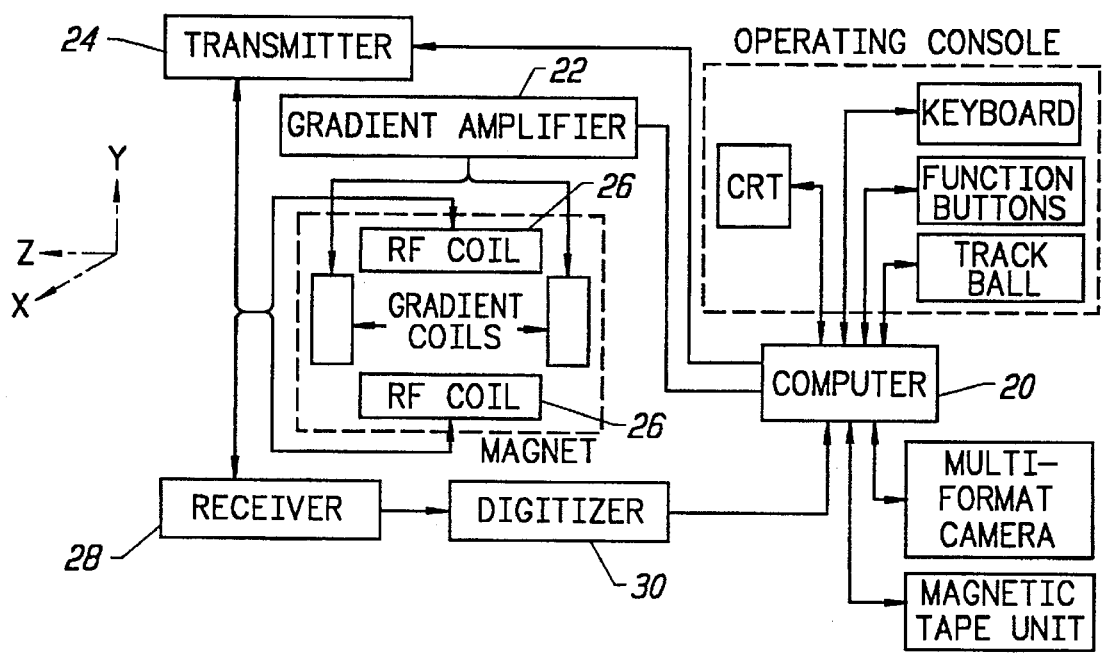
FIG. 2 is a functional block diagram of the MRI imaging apparatus of FIG. 1.

FIG. 2 is a functional block diagram of the imaging apparatus. A computer 20 is programmed to control the operation of the MRI apparatus and produce free induction decay (FID) signals detected therefrom. The gradient field is energized by a gradient amplifier 22, and the RF coils for impressing an RF magnetic moment at the Larmor frequency is controlled by the transmitter 24 and the RF coils 26. After the selected nuclei have been flipped, the RF coils 26 are employed to detect the FID signal which is passed to the receiver 28 and then through digitizer 30 for processing by computer 20.

The present invention combines a T2 weighted preparation sequence with an inversion recovery sequence which enables the suppression of a material having a particular T1 and T2 relaxation time. For example, given the similar spin-lattice relaxation of both muscle and blood, an inversion recovery sequence tailored to null muscle would also tend to null blood. However, since the spin—spin relaxation times of muscle and blood differ significantly, a late echo sequence enables the suppression of signals from muscle having the shorter T2 relaxation time. However, with large amounts of muscle compared to blood, the echo time must be made significantly long to suppress the muscle components significantly.

The invention combines a driven-equilibrium sequence with an inversion-recovery sequence to suppress a particular material depending on either or both its T1 and T2 relaxation times. Hence, it is useful in situations where there are two different species with similar T1 relaxation times (e.g., muscle and blood) but different T2 relaxation times. It can also be used in situations where there are two different species with similar T2 relaxation times but different T1 relaxation times. Alternatively, it can be used to simultaneously suppress two materials with different T1 and T2 relaxation times.

Figure 3:
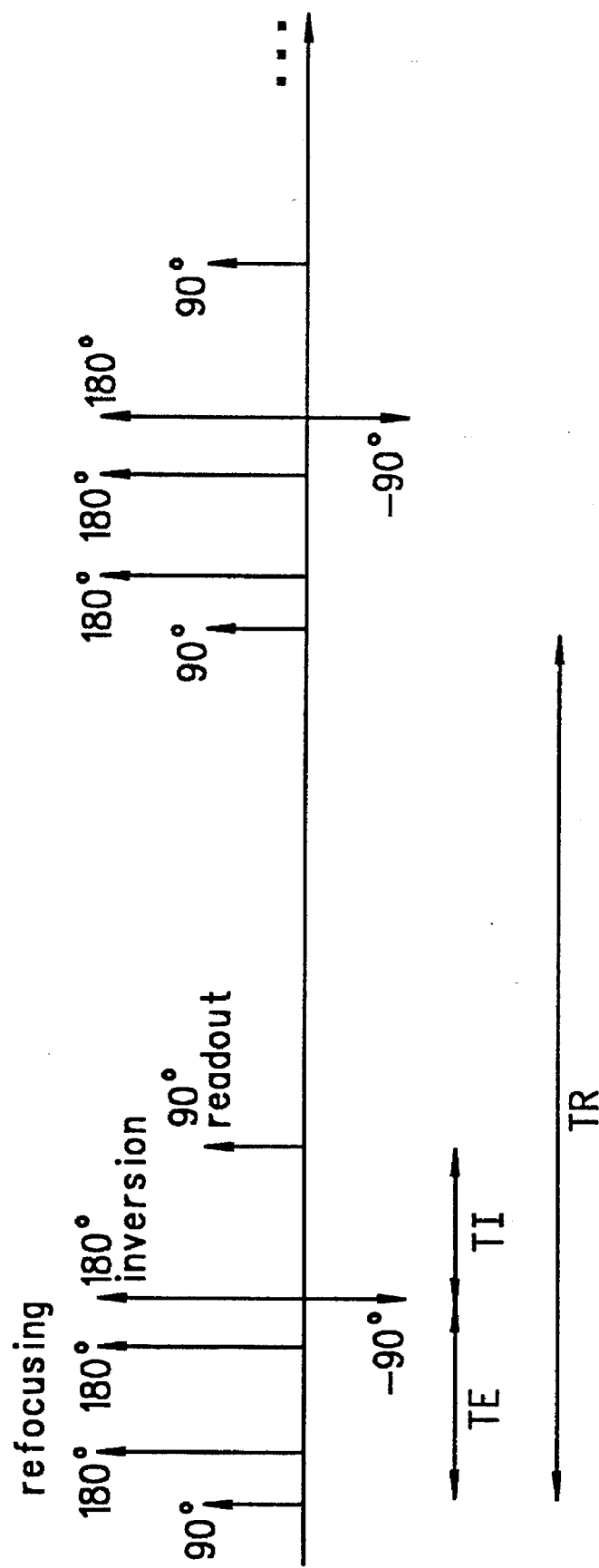
FIGS. 3–5 illustrate magnetic excitation pulses used in carrying out the invention in accordance with three embodiments.

The basic sequence in accordance with one embodiment is shown in FIG. 3. A 90° excitation tips all magnetization into the transverse plane, and a 180° refocusing pulse (or a series of 180° refocusing pulses) is then applied to produce a spin echo at time TE. At time TE, a −90° excitation pulse tips the magnetization back to the longitudinal axis. This driven-equilibrium sequence leads to a longitudinal magnetization of $M_o e^{-TE/T2}$, now dependent on TE and T2 but independent of T1. The −90° pulse is followed with a 180° excitation (either selective or nonselective) to invert the T2-weighted $M_Z$ component along the longitudinal axis. Following this inversion, the readout excitation is delayed by a time TI such that the material of concern is nulled or substantially reduced in magnetization during the inversion recovery. The readout excitation, typically a 90° pulse or other angle θ, tips longitudinal magnetization of the species to be imaged into the transverse plane for readout. The driven equilibrium sequence thus serves to alter the relative $M_Z$ components of similar T1 species so that the subsequent inversion nulling depends on the relaxation time for the material, T2.

For a single-shot application of this sequence (TR=∞), the longitudinal magnetization at the time of the readout excitation is $$M_o(1 - e^{-TI/T1} - e^{-TI/T1}e^{-TE/T2}) \quad (1)$$

A 90° readout excitation converts this longitudinal magnetization into transverse magnetization, thus producing a recordable signal.

More generally, if we take into account a repetition time TR between successive measurements, the resultant steady-state signal (with 90° readouts) is $$M_o(1 - e^{-TI/T1} - e^{-TI/T1}e^{-TE/T2} + e^{-TR/T1}e^{TE/T1}e^{-TE/T2}) \quad (2)$$

This can be rewritten as $$M_o(1 - E_i - E_i E_2 + E_1 E_a) \quad (3)$$

where $$E_i = e^{-TI/T1} \quad (4)$$

$$E_1 = e^{-TR/T1} \quad (5)$$

$$E_2 = e^{-TE/T2} \quad (6)$$

$$E_a = e^{TE/T1}e^{-TE/T2} = e^{-TE\cdot T1 - T2/T1 T2} \quad (7)$$

Given a TR, nulling a certain material requires that TE and TI be selected to make the above expression equal zero for the nulled material. Hence, given TR, T1 and T2, there exists a family of TI and TE values that achieve the desired suppression.

For comparison, it is interesting to note that the signal for an inversion-recovery signal (without the driven equilibrium part) is proportional to $$M_o(1 - 2E_i + E_1) \quad (8)$$

which implies that the nulling (or reduction) is independent of the material's T2.

Figure 4:
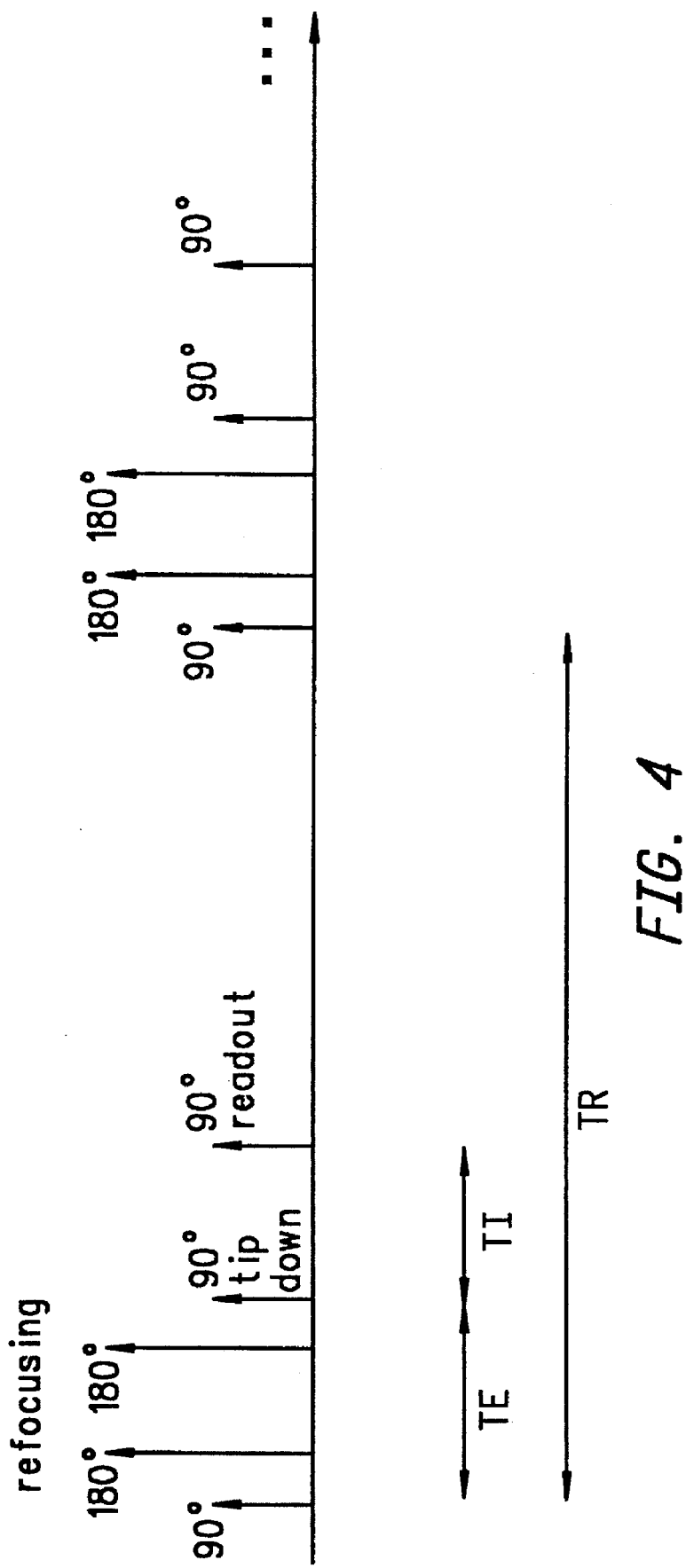

One modification to the above sequence that achieves similar performance is shown in FIG. 4 as follows: Instead of tipping up with a −90° pulse and applying a 180° inversion thereafter, one can simply tip the magnetization down towards the −Z axis at the echo time TE with a +90° excitation.

Figure 5:
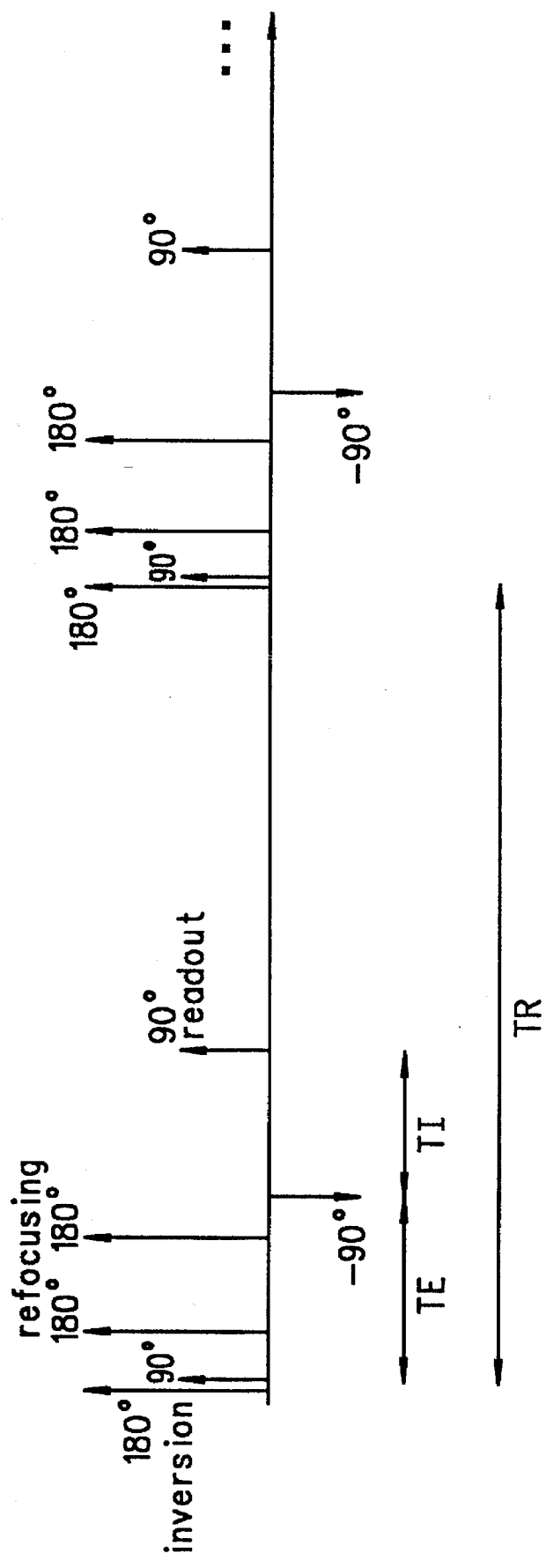

Another modification is to apply the inversion pulse just prior to the T2 weighted preparation sequence, as shown in FIG. 5. Therefore, the T2-weighted magnetization will get driven back to the −Z axis as desired instead of the +Z axis.

The pulses for the T2 weighted preparation sequence should be concerned with the practical considerations of $B_0$ and $B_1$ inhomogeneities. Compensated sequences such as those used by Brittain et al. (SMRM 1993) and in Brittain et al., "Coronary Angiography with Magnetization-Prepared T2 Contrast," MRM, Vol. 33, May 1995, pp. 689–696, could be employed for the T2 weighted preparation sequence. If used, the inversion pulse could be made adiabatic or quasi-adiabatic to offer better immunity to RF inhomogeneities. For the modified case where the tip-up/inversion is replaced by a +90° excitation, the +90° could be replaced by a composite excitation that offers immunity to RF inhomogeneities (e.g., 180°$_y$–[−90°$_x$]), assuming the initial excitation was a 90°$_x$).

The above expressions assume that the readout excitation is 90°. If we generalize the readout pulse to be an α pulse, then the steady state becomes $$\frac{M_o(1 - E_i - E_i E_2 + E_1 E_a)\sin\alpha}{1 + E_1 E_a \cos\alpha} \quad (9)$$

It will be noted that the nulling condition remains the same; i.e., it is independent of α. However, given a particular TE and TI that nulls a particular (T1, T2) species, we can maximize the signal for another (T1, T2) species. Differentiating the above expression with respect to α, and setting it to zero to determine the maximum, we find that the optimal angle $α_{opt}$ is $$\alpha_{opt} = \cos^{-1}(-E_t E_a) \qquad (10)$$

Figure 6:
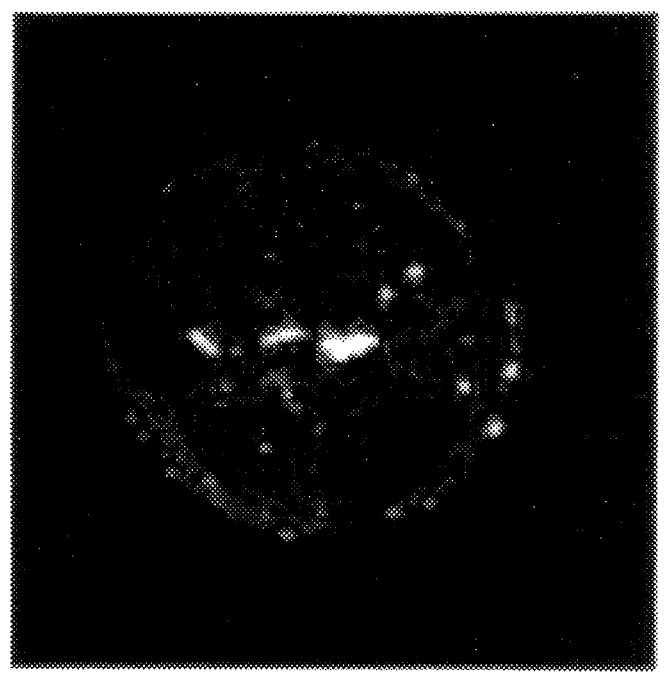
FIG. 6 is an axial section image of a human thigh in which blood is imaged and muscle is suppressed using the invention.

FIG. 6 is an axial section image of a human thigh in which blood is imaged while muscle is suppressed using the apparatus and method of the invention as reported by Brittain et al. in "Three-Dimensional Flow-Independent Peripheral Angiography," SMR 1995.

Although the described embodiments use the sequence for suppression of selected material, the sequence has value by itself for the type of contrast it produces between different (T1, T2) species. Thus, while the invention has been described with respect to specific embodiments and applications, the description is illustrative of the invention and is not to be construed as limiting the invention. For example, rather than using a single 180° inversion pulse to null a single species, multiple 180° inversion pulses can be used to null multiple species. As used herein, "null" includes "substantial reduction." Thus, various modifications and applications may occur to those skilled in the art without departing from the true spirit and scope of the invention as defined by the appended claims.

What is claimed is:

1. A method of selectively suppressing magnetic resonance signals in an object having at least two materials therein with different relaxation times, said method comprising the steps of
   a) positioning said object in a magnetic field along a longitudinal axis,
   b) applying a first excitation pulse to said object to tip nuclei spins into a transverse plane,
   c) applying at least one refocusing pulse to said object to produce a spin echo at a time TE, said spin echo including a magnetization component as a function of relaxation time,
   d) applying at least one pulse to said object to drive said spin echo to an inverted position along said longitudinal axis, and
   e) applying a readout excitation at a time TI when the longitudinal magnetization of one material is substantially reduced.

2. The method as defined by claim 1 wherein step d) includes the steps of
   applying an excitation pulse to said object to drive said spin echo to an uninverted position along said longitudinal axis, and
   applying another excitation pulse to said object to invert said magnetization component.

3. The method as defined by claim 2 wherein said first excitation pulse is a 90° pulse, in step c) said at least one refocusing pulse includes a 180° pulse, in step d) said excitation pulse is a −90° pulse, said another excitation pulse is a 180° pulse, and said readout excitation is a 90° pulse.

4. The method as defined by claim 1 wherein step d) includes applying a +90° pulse to said object.

5. The method as defined by claim 1 wherein said different relaxation times are spin-spin (T2) relaxation times.

6. The method as defined by claim 1 wherein said different relaxation times are spin-lattice (T1) relaxation times.

7. A method of selectively suppressing magnetic resonance signals in an object having at least two materials therein with different relaxation times, said method comprising the steps of
   a) positioning said object in a magnetic field along a longitudinal axis,
   b) applying an inversion pulse to invert nuclei spins,
   c) applying a first excitation pulse to said object to tip nuclei spins into a transverse plane,
   d) applying at least one refocusing pulse to said object to produce a spin echo at a time TE, said spin echo including a magnetization component as a function of relaxation time,
   e) applying at least one pulse to said object to drive said spin echo to an inverted position along said longitudinal axis, and
   f) applying a readout excitation at a readout time TI when the longitudinal magnetization of one material is substantially reduced.

8. Apparatus for use in magnetic resonance imaging of an object having at least two materials therein with different relaxation times, said apparatus comprising
   a) means for applying a static magnetic field through said object along a longitudinal axis,
   b) means for applying a first excitation pulse to said object to tip nuclei spins into a transverse plane,
   c) means for applying at least one refocusing pulse to said object to produce a spin echo at a time TE,
   d) means for applying at least one pulse to said object to drive said spin echo to an inverted position along said longitudinal axis,
   e) means for applying a readout excitation at a readout time when longitudinal magnetization of one material is substantially reduced, and
   f) means for detecting a readout signal.

9. Apparatus as defined by claim 8 wherein said d) means applies an excitation pulse to said object to drive said spin echo to an uninverted orientation along said longitudinal axis, and applies another excitation pulse to said object to invert said magnetization component.

10. Apparatus as defined by claim 9 wherein said first excitation pulse is a 90° pulse, in said c) element said at least one refocusing pulse includes a 180° pulse, in said d) element said excitation pulse is a −90° pulse, said another excitation pulse is a 180° pulse, and said readout excitation is a 90° pulse.

11. Apparatus as defined by claim 8 wherein said d) means applies a 90° pulse to said object.

12. Apparatus for use in magnetic resonance imaging of an object having at least two materials therein with different relaxation times, said apparatus comprising
   means for applying a static magnetic field through said object along a longitudinal axis,
   means for applying an inversion pulse to invert nuclei spins,
   means for applying a first excitation pulse to said object to tip nuclei spins into a transverse plane,
   means for applying at least one refocusing pulse to said object to produce a spin echo at a time TE, said spin echo including a magnetization component as a function of relaxation time,
   means for applying at least one pulse to said object to drive said spin echo to an inverted position along said longitudinal axis, and
   means for applying a readout excitation at a readout time TI when the longitudinal magnetization of one material is substantially reduced.

* * * * *